(12) United States Patent
Seidel

(10) Patent No.: US 7,799,579 B2
(45) Date of Patent: Sep. 21, 2010

(54) METHOD AND DEVICE FOR PROCESSING A BIOLOGICAL FLUID FOR ANALYTE DETERMINATION

(75) Inventor: Dietrich Seidel, Feldafing (DE)

(73) Assignee: Sebo GmbH, Erbach (DE)

( * ) Notice: Subject to any disclaimer, the term of this patent is extended or adjusted under 35 U.S.C. 154(b) by 406 days.

(21) Appl. No.: 11/822,287

(22) Filed: Jul. 3, 2007

(65) Prior Publication Data

US 2008/0038834 A1 Feb. 14, 2008

(30) Foreign Application Priority Data

Jul. 3, 2006 (EP) ............... 06 013 762
Jul. 25, 2006 (EP) ............... 06 015 470

(51) Int. Cl.
- G01N 30/02 (2006.01)
- G01N 1/28 (2006.01)
- G01N 33/48 (2006.01)
- G01N 35/10 (2006.01)

(52) U.S. Cl. ............... 436/174; 436/17; 436/161; 435/2; 73/61.41; 73/64.56

(58) Field of Classification Search ............... 436/174, 436/17, 161; 435/2; 73/61.41, 64.56
See application file for complete search history.

(56) References Cited

U.S. PATENT DOCUMENTS

| | | | | |
|---|---|---|---|---|
| 4,133,904 | A | * | 1/1979 | Steer et al. ............... 426/656 |
| 4,716,119 | A | | 12/1987 | Rehner et al. |
| 4,975,246 | A | * | 12/1990 | Charm ............... 422/21 |
| 5,334,499 | A | * | 8/1994 | Burdick et al. ............... 435/6 |
| 5,512,440 | A | | 4/1996 | Down et al. |
| 6,197,553 | B1 | | 3/2001 | Lee et al. |
| 6,579,706 | B2 | | 6/2003 | Grae |
| 6,623,945 | B1 | * | 9/2003 | Nair et al. ............... 435/173.4 |
| 2001/0051374 | A1 | | 12/2001 | Mclaughlin-Taylor et al. |
| 2002/0115201 | A1 | | 8/2002 | Barenburg et al. |
| 2004/0197788 | A1 | | 10/2004 | Daniel et al. |

OTHER PUBLICATIONS

Michal Markuszewski et al.; "Human red blood cells targeted metabolome anaylsis of glycolysis cycle metabolites by capillary electrophoresis using an indirect photometric detection method"; vol. 39; No. 3-4; Sep. 15, 2005; pp. 636-642; New York, NY, US.

Susanne Renner et al.; "Analysis of metabolites of glucose pathways in human erythrocytes by analytical isotachophoresis"; vol. 916; No. 1-2; May 4, 2001; pp. 247-253; Amsterdam, NL.

Waters, Larry C. et al., Microchip Device for Cell Lysis, Multiplex PCR Amplification, and Electrophoretic Sizing, Analytical Chemistry, Jan. 1, 1998, vol. 70, No. 1pp. 158-162.

Kurokawa, N. et al., "In-Vivo Distribution and Erythrocyte Binding Characteristics of Cyclosporin in Renal Transplant Patients." J. Pharm. Pharmacol. 1996, vol. 48, pp. 553-559.

Trepanier, Daniel J. et al., "Rapamycin: Distribution, Pharmacokinetics and Therapuetic Range Investigations: An Update." Clinical Biochemistry, 1998, vol. 31, No. 5, pp. 345-351.

Zahir, H. et al., "Validation of methods to study the distribution and protein binding of tacrolimus in human blood." Journal of Pharmacological and Toxicological Methods 46 (2001) pp. 27-35.

Ham, Thomas Hale et al., "Studies on the Destruction of Red Blood Cells. IV: Thermal Injury: Action of Heat in Causing Increased Spheroidicity, Osmotic and Mechanical Fragilities and hemolysisi of Erythorocytes; Observationso on the Mechanisms of Destruction of Such Erythrocytes in Dogs and in a Patient with a Fatal Thermal Burn." www.bloodjournal.org at UBM Biblotheck Grosshadern, Blood, 1948 Feb. 21, 2008 31, pp. 373-403.

\* cited by examiner

Primary Examiner—Jill Warden
Assistant Examiner—Dwan A Gerido
(74) Attorney, Agent, or Firm—Arent Fox LLP

(57) ABSTRACT

The present invention refers to a method of processing a biological fluid which comprises cellular components by heat treatment. The method is particularly useful for preparing biological samples for analyte detection. Further, the invention refers to a processed biological fluid comprising substantially quantitatively disintegrated cellular components.

40 Claims, No Drawings

METHOD AND DEVICE FOR PROCESSING A BIOLOGICAL FLUID FOR ANALYTE DETERMINATION

The present invention refers to a method and device for processing a biological fluid which comprises cellular components by heat treatment. The method is particularly useful for preparing biological samples for analyte detection. Further, the invention refers to a processed biological fluid comprising substantially quantitatively disintegrated cellular components.

The determination of analytes in samples from biological fluids often requires complicated and tedious pretreatment procedures in order to remove cellular components from the fluid sample. For example, whole blood contains components, namely erythrocytes, leukocytes and thrombocytes. In order to determine analytes in a blood sample, these cellular components often have to be removed by pre-treatment procedures such as centrifugation, filtration, sedimentation and/or homogenized by lysis using chemical reagents or mechanical treatment. These procedures, however, are often difficult to integrate into an automated test format. This holds also for a situation in which the target analytes are present in the cellular components, e.g. immuno-suppressive drugs in erythrocytes. In this case, the cellular components either are isolated or enriched by centrifugation and/or filtration prior to the addition of a lysis reagent or they are denatured by addition of a denaturing agent to the original sample, for example a mixture of $ZnSO_4$ and acetonitrile, or the original sample is treated with temperatures of $-20$ to $-170°$ C.

An object of the present invention was to provide an improved method for processing biological fluids which does not have the disadvantages associated with prior art procedures.

A first aspect of the present invention is a method of processing a biological fluid which comprises cellular components, wherein the fluid is subjected to a heat treatment under conditions
(i) to provide substantially quantitative disintegration of said cellular components and
(ii) not to cause substantial sedimentation, precipitation, denaturation, agglutination and gelation of fluid components.

A further aspect of the present invention is a processed biological fluid comprising substantially quantitatively disintegrated cellular components which is substantially free from sedimentation, precipitation, denaturation, agglutination and gelation products.

Still a further aspect of the present invention is a method of determining an analyte in a biological fluid sample, wherein the biological fluid is processed as described above and the analyte is determined in the processed biological fluid.

Still a further aspect of the present invention is a device for processing a biological fluid, which comprises cellular components comprising:
(a) a fluid introduction port,
(b) a fluid processing conduit, which is at least partially heatable,
(c) a heating element for heating a predetermined part of the fluid processing conduit,
(d) a fluid transportation element, e.g. a pumping element,
(e) a control element for controlling the heating of the fluid under conditions
  (i) to provide substantially quantitative disintegration of said cellular components and
  (ii) not to cause substantial sedimentation, precipitation, denaturation, agglutination and gelation of fluid components.
(f) optionally a cleaning element and
(g) optionally a sample analyzing element.

Surprisingly, the present inventor has found that a complete disintegration of cellular components, preferably cells or cell clusters from higher organisms, more preferably animal cells such as mammalian cells including human cells, and most preferably blood cells such as erythrocytes, leukocytes and/or thrombocytes in biological samples may be achieved by heat treatment under predetermined conditions of time and temperature. By means of this heat treatment, the cellular components contained in a biological fluid are disintegrated without substantial sedimentation, precipitation, denaturation, agglutination and/or gelation of fluid components.

The heat treatment may be carried out at a temperature of from 60-90° C., preferably from 60-75° C. and more preferably from 65-70° C. The heat treatment is carried out for a time sufficient to achieve a desired disintegration at the chosen treatment temperature. Preferably, the heat treatment is carried out for a time of 5 sec to 1 min, more preferably from 10 sec to 40 sec. Especially preferred is a temperature of 70° C. for 30-40, e.g. 35 sec. The heat treatment may be carried out in any suitable container, e.g. a glass-capillary (55×0.5 mm inner diameter).

In Table 1, suitable conditions for the heat treatment of a whole blood sample with a given erythrocyte count, optionally supplemented with organic solvents and/or plasma of blood group AB are shown. These temperature/time conditions are defined by an upper time limit (indicated as value tmax) at a given temperature and by a lower time limit (indicated as value tmin) at a given temperature. If the heat treatment is carried out for a time period longer than the tmax value, gelation occurs. If the heat treatment period is shorter than the tmin value, only incomplete disintegration occurs. If other fluids, e.g. organic solvents and/or aqueous fluids, e.g. plasma, are added to the sample before heat treatment, the values of tmax and tmin may vary as shown in Tables 2-6.

The gelation of the sample may be determined by an increase in viscosity. The completeness of disintegration may be determined by cell counting, e.g. in a Neubauer counting chamber, by microscopic inspection for particular components and/or by lack of sediment formation after centrifugation. In this context, it should be noted that about 95% of cellular blood components are represented by erythrocytes. Thus, the cell count in a blood sample is preferably determined by counting the erythrocytes.

By means of the present invention the cell count in the sample is preferably reduced to 0.1% or less and more preferably to 0.01% or less of the original value. For example, when subjecting a sample with $5 \times 10^6$ erythrocytes per μl to heat treatment, the cell count is preferably reduced to $5 \times 10^3$ cells or less per μl (cf. Example 1), more preferably to 500 cells or less per μl. Most preferably, the sample is free from detectable cells. The absence of particular components may also be determined by light-microscopic observation, e.g. up to 100× magnification, and/or by centrifugation for 10 min at up to 3000 g, preferably at up to 7400 g.

The heat treatment may be carried out when the fluid is kept static, e.g. while the fluid is in a reaction vessel. In a preferred embodiment, however, particularly for automated operations, the heat treatment may be carried out while the fluid is in flow, e.g. while the fluid is passed through a conduit. The heat treatment in a flowing system may be carried out while passing the sample fluid through a heated conduit, e.g. a capillary conduit, preferably with an inner diameter of about 0.1-0.8 mm, for example of about 0.5 mm with a predetermined flow rate, wherein the conduit has a predetermined length in order to achieve the desired residence time within the heated conduit. The heating may be carried out by any suitable means and may comprise e.g. inductive heating such as microwave treatment, for example as described in U.S. Pat. No. 6,605,454, convective heating, resistive heating and/or heating by laser excitation.

The biological fluid may be a body fluid such as whole blood, urine, cerebrospinal fluid, saliva, lymph fluid etc. or fluid from a cell culture or any other biological fluid comprising cellular components, particularly fluids comprising blood cells. More preferably, the biological fluid is whole blood, such as venous, arterial or capillary blood, particularly anticoagulant-treated whole blood, e.g. EDTA-, citrate-, or heparin-treated whole blood. For example, a sample may be taken with an anticoagulant containing blood withdrawal device and directly subjected to further processing as described below.

The sample volume may be varied broadly, e.g. in the range of 1 nl or more, preferably 10 nl or more and up to 1 ml. Thus, the method is suitable for miniaturized applications, e.g. microfluidic devices on chip format, nano LC-MS analysis etc.

The method of the present invention does not require sedimentation and/or precipitation and/or centrifugation steps and/or the addition of chemical lysis and/or disintegration reagents. Thus, the heat treatment is preferably carried out without previous removal and/or lysis of cellular components. The method may be carried out in any suitable device, e.g. a single-use device or a reusable device. Preferably, the method is an automated procedure, which may be carried out in an integrated device, i.e. a device into which the fluid sample is transferred, optionally after mixing, e.g. with a further fluid, without pretreatment, particularly without removal and/or lysis of cellular components. Within the device, the sample is preferably directly subjected to the treatment without prior removal and/or a lysis of cellular components. After treatment, subsequent steps, e.g. an analyte determination may be carried out. Most preferably, the heat treatment is carried out with a substantially native sample, e.g. a sample comprising substantially intact cellular components such as whole blood.

The method of the present invention may include the addition of further fluid to the biological fluid before and/or after processing. The further fluid may be an organic solvent, preferably in an amount of up to 20% (vol/vol), more preferably in an amount of up to 10% (vol/vol) based on the volume of the biological fluid. The organic solvent is preferably selected from water-miscible solvents such as methanol, ethanol, acetonitrile, dimethylsulfoxide, and combinations thereof. The addition of organic solvents may have an influence on the temperature/time conditions for the heat treatment as shown in Tables 2 and 3.

Preferably, the further fluid does not substantially effect lysis of cellular components. More preferably, the further fluid is an aqueous fluid, e.g. an aqueous buffer solution or a further biological fluid, preferably having a ionic strength corresponding to 0.5-1.4% NaCl, more preferably 0.7-1.2% NaCl and most preferably about 0.9% NaCl. Preferably, the aqueous fluid is a biological fluid without cellular components such as plasma. More preferably, the plasma is plasma of the blood group AB. The further aqueous fluid may comprise an organic solvent, e.g. in an amount of up to 20% (vol/vol), preferably up to 10% (vol/vol) based on the volume of the second biological fluid such as methanol, ethanol, acetonitrile, dimethylsulfoxide and/or combinations thereof.

The second biological fluid is preferably added in a volume ratio of 5:1 to 1:10 based on the volume of the first biological fluid. Preferably, the second fluid is added before the heat treatment. The addition of the second fluid may influence the suitable temperature/time conditions for the heat treatment step as shown in Tables 4-6. Surprisingly, it was found that addition of AB plasma, optionally with an organic solvent, actually increases the suitable treatment time range at a given temperature.

The further fluid may be a standardisation and/or calibrator fluid comprising a predetermined amount of at least one standardisation and/calibrator compound. The addition of standardisation and/or calibrator compounds is particularly suitable if the heat-treated biological fluid is further analysed by means of chromatographic, spectrometric and/or spectroscopic methods. The standardisation and/or calibrator compounds may be analyte analogues which contain stable isotopes such as $^2H$ and/or $^{13}C$ and thus may be detected by mass spectrometry.

The method also may include the addition of a marker/staining compound for lipids, proteins, peptides, nucleic acids and carbohydrates to the biological fluid before and/or after processing.

A further aspect of the present invention refers to a composition comprising AB plasma, an organic solvent in an amount of up to 20% (vol/vol), preferably up to 10% (vol/vol) based on the volume of the plasma, such as methanol, ethanol, acetonitrile and/or dimethylsulfoxide and a predetermined amount of at least one standardisation and/or calibrator compound. The compound may be used as a standardisation and/or calibrator fluid, particularly in combination with the heat treatment procedure as described above.

Still a further aspect of the present invention refers to a processed biological fluid which is obtainable as described above. The processed fluid represents a novel matrix which is particularly suitable for clinical testing. The processed fluid is stable at least 1 week, preferably at least 2 weeks at 4° C. and/or at least 1 day, preferably at least 5 days, at 25° C. Thus, the handling of the processed fluid is much more uncomplicated compared to a non-treated whole blood sample. The term "stable" particularly means that sedimentation does not occur.

The processed biological fluid comprises substantially quantitatively disintegrated cellular components such as components from blood cells. The processed fluid is substantially free from sedimentation, precipitation, denaturation, agglutination and/or gelation products. In a preferred embodiment, the invention refers to a processed fluid which substantially (i) is free from particular components on microscopic observation (e.g. 100× magnification);
(ii) is free from sediment after centrifugation for 10 min. at up to 3000 g, preferably at up to 7400 g and/or
(iii) is free from cells as determined in a cell counting chamber.

The processed fluid preferably has a ionic strength corresponding to 0.5-1.4% NaCl, more preferably 0.7-1.2% NaCl and most preferably a substantially physiological salt concentration. The processed fluid may be free from added disintegration and/or lysis reagents and/or detergents. On the other hand, the processed fluid may also comprise organic solvents and/or added aqueous fluid such as plasma of blood group AB as described above. Most preferably, the processed fluid is processed whole blood.

The present invention also refers to a method of determining an analyte in a biological fluid sample which has been subjected to a heat treatment as described above. The analyte may be any analyte which may be detected in biological fluids, e.g. a biological compound such as a nucleic acid, a polypeptide, peptide, lipid, sugar, hormone, metabolite, etc. On the other hand, the analyte may be a non-biological compound, e.g. a pharmaceutical compound. In a preferred embodiment, the analyte is an immunosuppressive drug, such as cyclosporin, rapamycin or tacrolimus or related compounds.

The analyte determination in the processed fluid may be carried out according to any known method. For example, the analyte determination may be carried out according to chemical, biochemical and/or physicochemical methods and may comprise a hybridization reaction, an immunological reaction, an enzymatic reaction, e.g. a nucleic acid amplification, a chromatographic analysis, a spectrometric analysis, such as a mass-spectrometric or a NMR analysis and/or a spectroscopic analysis. In an especially preferred embodiment, the invention refers to a method of determining an immunosuppressive drug in a whole blood sample, wherein the whole blood is processed by a heat treatment as described above and the immunosuppressive drug is determined in the processed whole blood according to standard methods, e.g. by mass-spectrometric methods.

In a further preferred embodiment, the analyte is a clinical-chemical parameter, e.g. a clinical-chemical parameter associated with an inborn metabolic disorder, e.g. phenylketonuria. In this embodiment, the sample is preferably a capillary blood sample which may be obtained from newborns.

In a still further preferred embodiment, the method is suitable for processing blood samples from non-human animals, preferably mice, guinea pigs and rats. For example, the samples may be taken by automated systems and directly processed as described above. A preferred automated system is the Accu Sampler® from DiLab®.

A device of the present invention may comprise a fluid introduction port, where a sample of a biological fluid may e.g. be injected into the device. The fluid is transported within the device by a fluid transportation element, e.g. a pumping element. Further, the device may comprise a fluid processing conduit which is at least partially heatable. The heatable part of the fluid processing conduit may be an integral part of the device or removably attached to the device. The fluid processing conduit has preferably an inner diameter of about 0.1-0.8 mm. In order to achieve a desired residence time within heatable portion of the conduit a predetermined flow rate of the biological fluid may be adjusted. The heating element may be any suitable heating element, e.g. an element for inductive heating, an element for convective heating, an element for resistive heating and/or an element for heating by laser excitation. For example, the heating element may be a heating coil wrapped around a predetermined part of the fluid processing conduit or a microwave emitter. The control element provides control of the sample processing, particularly the heating of the fluid, e.g. by controlling the heating intensity and/or time and/or the fluid flow rate in the heatable part of the fluid processing conduit.

The device may optionally comprise a cleaning element which is suitable for cleaning the fluid processing conduit or at least a part thereof. For example, the cleaning element is adapted for carrying out a cleaning of the fluid processing conduit or a part thereof after a predetermined number of biological fluid processing cycles. Preferably, the cleaning comprises passing a cleaning fluid through the fluid processing conduit or a part thereof. The cleaning fluid is capable of removing biological, e.g. proteinaceous residues in the processing conduit. Preferably, the cleaning fluid is an alkaline hypochlorite solution, e.g. an alkaline NaOCl solution. The cleaning may involve flushing of the fluid processing conduit or a part thereof with the cleaning fluid, wherein the cleaning fluid is preferably at an elevated temperature, e.g. at a temperature of $T \geqq 60°$ C. The cleaning efficacy may be controlled by monitoring the presence of biological materials in the fluid processing conduit or a part thereof after a cleaning procedure. The monitoring preferably comprises a photometric detection of biological material, e.g. proteinaceous material. The detection may be carried out by determining biological materials, which have been solubilised/hydrolysed by the cleaning fluid, preferably in an online detection mode. Biological materials may be determined by a suitable colour reaction, e.g. the OPA reaction wherein O-phthaldialdehyde and N,N-dimethyl-2-mercaptoethyl-ammonium chloride may react with primary amine compounds, e.g. proteins or hydrolysis products, under alkaline conditions (e.g. 0.1 mol/l $Na_2B_4O_7$ pH 9.3) to an 1-alkylthio-2-alkylisoindole, which may be photometrically detected at 340 nm.

Further, the device optionally comprises a sample analysing element. The sample analysing element may be any element which is suitable for analyte detection in a biological sample. Preferably, the sample analysing element comprises a chromatographic element, e.g. an HPLC element, an extraction element, e.g. a Solid Phase Extraction (SPE) element, a spectrometric element, e.g. a mass-spectrometric or NMR element, a spectroscopic element, an enzymatic and/or immunoassay element and/or a hybridization assay element.

Finally, the device may comprise a processor unit which may transfer data to and/or receive data from a remote control unit. The data transfer may occur online, e.g. by wireless transfer such as via GSM/GPRS/3G data transfer. The remote control unit may be adapted to authorise fluid processing for a respective device, e.g. after payment for carrying out a predetermined number of fluid processing procedures has been received (i.e. pay-per-process).

Further, the present invention is explained in more detail by the following examples.

EXAMPLE 1

Heat Treatment of Blood Samples (Static System)

A glass-capillary (55 mm length×0.5 mm inner diameter) is filled with about 10 µl of a blood sample (erythrocytes: $5.18 \times 10^6$/µl; hemoglobin: 17.5 g/dl; hematocrite 50.1%), sealed at one end with plasticine and heated in a thermostated water-bath at a given temperature for a given time. At the end of the heating process the glass-capillary is immediately immersed in an ice-bath (4° C.). The plasticine sealing is cut off, the glass-capillary is emptied and the treated blood sample is further investigated for gelation and completeness of blood cell disintegration. The parameter $t_{max}$ is defined as the heating time [sec] at which gelation of the sample occurs minus 1 second. The parameter $t_{min}$ is defined as the minimal heating time at which no erythrocytes are detected using a Neubauer counting chamber.

EXAMPLE 2

Erythrocyte Count

To 10 µl of whole blood or treated blood 990 µl of Hayemsch-solution (Merck KGaA, Darmstadt, Germany) are added. The mixture is vortexed and an aliquot is introduced into a Neubauer counting chamber. The erythrocytes present in 5 defined squares are counted using a microscope and a magnification of 100.

Calculation:

$$\text{Erythrocytes}/\mu l \text{ (sample)} = \frac{\text{Number of erythrocytes counted} \times 100}{0.2 \text{ mm}^2 \times 0.1 \text{ mm}}$$

The results are shown in the following Tables 1-6.

TABLE 1

Heat treatment of whole blood (erythrocytes: $5.18 \times 10^6/\mu l$; hemoglobin: 17.5 g/dl; hematocrite 50.1%).

| Temperature [° C.] | $t_{max}$ [sec] | $t_{min}$ [sec] |
|---|---|---|
| 90 | 3 | 3 |
| 85 | 5 | 4 |
| 80 | 9 | 5 |
| 75 | 23 | 9 |
| 70 | 48 | 21 |
| 65 | 242 | 33 |
| 60 | 802 | 349 |

TABLE 2

Heat-treatment of whole blood containing 5 vol % of methanol

| Temperature [° C.] | $t_{max}$ [sec] | $t_{min}$ [sec] |
|---|---|---|
| 80 | 6 | 6 |
| 75 | 13 | 7 |
| 70 | 42 | 11 |
| 65 | 169 | 18 |
| 60 | 646 | 21 |

TABLE 3

Heat-treatment of whole blood containing 5 vol % of acetonitrile

| Temperature [° C.] | $t_{max}$ [sec] | $t_{min}$ [sec] |
|---|---|---|
| 80 | 6 | 5 |
| 75 | 10 | 9 |
| 70 | 21 | 10 |
| 65 | 49 | 11 |
| 60 | 184 | 32 |

TABLE 4

Heat-treatment of a 1:1 mixture of whole blood and AB-plasma

| Temperature [° C.] | $t_{max}$ [sec] | $t_{min}$ [sec] |
|---|---|---|
| 80 | 15 | 8 |
| 75 | 31 | 9 |
| 70 | 65 | 41 |
| 65 | 412 | 66 |

TABLE 5

Heat-treatment of a 1:1 mixture of whole blood and AB-plasma containing 5 vol % of methanol

| Temperature [° C.] | $t_{max}$ [sec] | $t_{min}$ [sec] |
|---|---|---|
| 80 | 5 | 3 |
| 75 | 13 | 3 |
| 70 | 38 | 3 |
| 65 | 126 | 8 |
| 60 | 693 | 28 |

TABLE 6

Heat-treatment of a 1:1 mixture of whole blood and AB-plasma containing 2.5, 5 or 10 vol % acetonitrile

| Temperature [° C.] | $t_{max}$ [sec] acetonitrile vol % | | | $t_{min}$ [sec] acetonitrile vol % | | |
|---|---|---|---|---|---|---|
| | 2.5 | 5 | 10 | 2.5 | 5 | 10 |
| 80 | 11 | 5 | 3 | 5 | 4 | 1 |
| 75 | 23 | 11 | 4 | 3 | 2 | 1 |
| 70 | 41 | 24 | 5 | 4 | 5 | 1 |
| 65 | 171 | 53 | 17 | 10 | 12 | 1 |
| 60 | 753 | 281 | 35 | 11 | 33 | 2 |

EXAMPLE 3

Heat Treatment of a Blood Sample (Flow System)

For the treatment of a blood sample (e.g. 10 μl) using a heated stainless-steel capillary with the dimension of 0.5 mm internal diameter and 300 mm in length, the heating time at a given temperature can be preadjusted via the flow-rate of a given test fluid such as 0.9 vol % NaCl solution.

For a temperature of 75° C. the minimal capillary retention time $t_{min}$ of 9 sec (cf. Example 1, Table 1) is reached with a flow-rate of 466 μl/min and the maximal capillary retention time $t_{max}$ of 23 sec. (cf. Example 1, Table 1) is reached with a flow-rate of 183 μl/min. Thus, a preferred flow-rate for such a sample size and capillary configuration would be within these boundaries, e.g. amounting to approximately 325 μl/min. This flow-rate is also optimal for electrospray-ionisation in mass spectrometry.

Calculation:

$$\text{Flow rate } [\mu l/\text{min}] = \frac{\text{Volume Capillary } [\mu l] + \text{Volume Sample } [\mu l]}{t_{\min} (\text{or } t_{\max}) \text{ [sec]}} \times 60$$

The invention claimed is:

1. A method of conducting a heat treatment of a biological fluid which comprises cellular components, comprising:
   heating the biological fluid to a temperature of from 60-90° C.; and
   maintaining the temperature of the biological fluid for a period of from 10 seconds to 40 seconds;
   wherein the fluid is subjected to the heat treatment under conditions
   (i) to provide substantially quantitative disintegration of said cellular components and
   (ii) not to cause substantial sedimentation, precipitation, denaturation, agglutination and gelation of fluid components.

2. The method of claim 1 wherein the heat treatment is carried out at a temperature of from 60-75° C.

3. The method of claim 1 wherein the heat treatment is carried out while the fluid is static.

4. The method of claim 1 wherein the heat treatment is carried out using a heating method selected from the group consisting of inductive heating, convective heating, resistive heating and heating by laser excitation.

5. The method of claim 1 wherein the biological fluid is a body fluid or a cell culture fluid.

6. The method of claim 1 which does not include
   (i) a sedimentation and/or precipitation step and/or centrifugation step and/or
   (ii) an addition of chemical disintegration and/or lysis reagents.

7. The method of claim 1 which is carried out as an automated procedure.

8. The method of claim 1 further comprising adding a further fluid to the biological fluid before and/or after said heat treatment.

9. The method of claim 1 wherein the biological fluid is whole blood.

10. A processed biological fluid obtained by the method of claim 1.

11. The processed fluid of claim 10 comprising substantially quantitatively disintegrated cellular components which is substantially free from sedimentation, precipitation, denaturation, agglutination and gelation products.

12. The processed fluid of claim 10 which substantially
   (i) is free from particulate components on microscopic observation;
   (ii) is free from sediment after centrifugation; and/or
   (iii) is free from cells as determined in a cell counting chamber.

13. A method of conducting a heat treatment of a biological fluid which comprises cellular components, comprising:
   heating the biological fluid to a temperature of from 60-90° C.; and
   maintaining the temperature of the biological fluid for a period of from 5 seconds to 1 minute;
wherein the fluid is subjected to the heat treatment under conditions
   (i) to provide substantially quantitative disintegration of said cellular components and
   (ii) not to cause substantial sedimentation, precipitation, denaturation, agglutination and gelation of fluid components,
   wherein the heat treatment is carried out while the fluid is in flow.

14. A method of conducting a heat treatment of a biological fluid which comprises cellular components, comprising:
   heating the biological fluid to a temperature of from 60-90° C.; and
   maintaining the temperature of the biological fluid for a period of from 5 seconds to 1 minute;
wherein the fluid is subjected to the heat treatment under conditions
   (i) to provide substantially quantitative disintegration of said cellular components and
   (ii) not to cause substantial sedimentation, precipitation, denaturation, agglutination and gelation of fluid components,
   wherein the method further comprises adding a further fluid to the biological fluid before and/or after said heat treatment, and the further fluid comprises an organic solvent in an amount of up to 20% (vol/vol) based on the volume of the biological fluid, and wherein the further fluid is selected from the group consisting of methanol, ethanol, acetonitrile and dimethylsulfoxide.

15. A method of conducting a heat treatment of a biological fluid which comprises cellular components, comprising:
   heating the biological fluid to a temperature of from 60-90° C.; and
   maintaining the temperature of the biological fluid for a period of from 5 seconds to 1 minute;
wherein the fluid is subjected to the heat treatment under conditions
   (i) to provide substantially quantitative disintegration of said cellular components and
   (ii) not to cause substantial sedimentation, precipitation, denaturation, agglutination and gelation of fluid components,
   wherein the method further comprises adding a further fluid to the biological fluid before and/or after said heat treatment, and the further fluid comprises an aqueous fluid without cellular components, wherein the aqueous fluid optionally further comprises an organic solvent in an amount of up to 20% (vol/vol) based on the volume of the aqueous fluid.

16. The method of claim 15 wherein the aqueous fluid without cellular components is plasma.

17. A method of conducting a heat treatment of a biological fluid which comprises cellular components, comprising:
   heating the biological fluid to a temperature of from 60-90° C.; and
   maintaining the temperature of the biological fluid for a period of from 5 seconds to 1 minute;
wherein the fluid is subjected to the heat treatment under conditions
   (i) to provide substantially quantitative disintegration of said cellular components and
   (ii) not to cause substantial sedimentation, precipitation, denaturation, agglutination and gelation of fluid components,
   wherein the method further comprises adding a further fluid to the biological fluid before and/or after said heat treatment, and the further fluid is a standardization and/or calibrator fluid comprising a predetermined amount of at least one standardization and/or calibrator compound.

18. A processed biological fluid obtained by conducting a heat treatment of a biological fluid which comprises cellular components, comprising:
   heating the biological fluid to a temperature of from 60-90° C.; and
   maintaining the temperature of the biological fluid for a period of from 5 seconds to 1 minute;
wherein the fluid is subjected to the heat treatment under conditions
   (i) to provide substantially quantitative disintegration of said cellular components and
   (ii) not to cause substantial sedimentation, precipitation, denaturation, agglutination and gelation of fluid components,
wherein the processed biological fluid has a substantially physiological salt concentration.

19. A processed biological fluid obtained by conducting a heat treatment of a biological fluid which comprises cellular components, comprising:
   heating the biological fluid to a temperature of from 60-90° C.; and
   maintaining the temperature of the biological fluid for a period of from 5 seconds to 1 minute;
wherein the fluid is subjected to the heat treatment under conditions
   (i) to provide substantially quantitative disintegration of said cellular components and
   (ii) not to cause substantial sedimentation, precipitation, denaturation, agglutination and gelation of fluid components,
wherein the processed biological fluid is free from added reagents.

20. A processed biological fluid obtained by conducting a heat treatment of a biological fluid which comprises cellular components, comprising:
   heating the biological fluid to a temperature of from 60-90° C.; and
   maintaining the temperature of the biological fluid for a period of from 5 seconds to 1 minute;
wherein the fluid is subjected to the heat treatment under conditions
   (i) to provide substantially quantitative disintegration of said cellular components and
   (ii) not to cause substantial sedimentation, precipitation, denaturation, agglutination and gelation of fluid components,
wherein the processed biological fluid is cell-disintegrated blood.

21. A method of conducting a heat treatment of a biological fluid which comprises cellular components, wherein the biological fluid comprises whole blood, wherein the fluid is subjected to the heat treatment under conditions
   (i) that provide substantially quantitative disintegration of said cellular components; and
   (ii) that do not cause substantial sedimentation, precipitation, denaturation, agglutination and gelation of fluid components,
   wherein the heat treatment is carried out under conditions of temperature and time defined by an upper time limit at a given temperature and by a lower time limit at a given temperature, and wherein, when the heat treatment is carried out for a time period longer that the upper time limit, gelation occurs, and wherein, when the heat treatment is carried out for a time period shorter than the lower time limit, incomplete disintegration occurs, and wherein the cell count in the biological fluid is reduced to 0.1% or less.

22. The method of claim 21 wherein the heat treatment is carried out at a temperature of from 60-90° C.

23. The method of claim 21 wherein the heat treatment is carried out for a time of 5 sec to 1 minute.

24. The method of claim 21 wherein the heat treatment is carried out while the fluid is static.

25. The method of claim 21 wherein the heat treatment is carried out while the fluid is in flow.

26. The method of claim 21 wherein the heat treatment is carried out using a heating method selected from the group consisting of inductive heating, convective heating, resistive heating and heating by laser excitation.

27. The method of claim 21 wherein the biological fluid comprises anti-coagulant treated whole blood.

28. The method of claim 21 which does not include
   (i) a sedimentation and/or precipitation step and/or centrifugation step and/or
   (ii) an addition of chemical disintegration and/or lysis reagents.

29. The method of claim 21 which is carried out as an automated procedure.

30. The method of claim 21 further comprising adding a further fluid to the biological fluid before and/or after said heat treatment.

31. The method of claim 30 wherein the further fluid is an organic solvent in an amount of up to 20% (vol/vol) based on the volume of the biological fluid, and wherein the further fluid is selected from the group consisting of methanol, ethanol, acetonitrile and dimethylsulfoxide.

32. The method of claim 30 wherein the further fluid is a standardization and/or calibrator fluid comprising a predetermined amount of at least one standardization and/or calibrator compound.

33. The method of claim 30 wherein the further fluid is an aqueous fluid without cellular components, wherein the aqueous fluid optionally further comprises an organic solvent in an amount of up to 20% (vol/vol) based on the volume of the aqueous fluid.

34. The method of claim 33 wherein the aqueous fluid without cellular components is plasma.

35. A processed biological fluid obtained by the method of claim 21.

36. The processed fluid of claim 35 comprising substantially quantitatively disintegrated cellular components which is substantially free from sedimentation, precipitation, denaturation, agglutination and gelation products.

37. The processed fluid of claim 35 which substantially
   (i) is free from particulate components on microscopic observation;
   (ii) is free from sediment after centrifugation; and/or
   (iii) is free from cells as determined in a cell counting chamber.

38. The processed fluid of claim 35 which has a substantially physiological salt concentration.

39. The processed fluid of claim 35 which is free from added reagents.

40. The processed fluid of claim 35 which is cell-disintegrated blood.

* * * * *